(12) United States Patent
Winder et al.

(10) Patent No.: US 7,429,249 B1
(45) Date of Patent: Sep. 30, 2008

(54) METHOD FOR CAVITATION-INDUCED TISSUE HEALING WITH LOW INTENSITY ULTRASOUND

(75) Inventors: Alan A. Winder, Westport, CT (US); Roger J. Talish, Hillsborough, NJ (US)

(73) Assignee: Exogen, Inc., Piscataway, NJ (US)

( * ) Notice: Subject to any disclaimer, the term of this patent is extended or adjusted under 35 U.S.C. 154(b) by 0 days.

(21) Appl. No.: 09/980,329

(22) PCT Filed: Jun. 14, 2000

(86) PCT No.: PCT/US00/16471

§ 371 (c)(1),
(2), (4) Date: Mar. 5, 2002

(87) PCT Pub. No.: WO00/76406

PCT Pub. Date: Dec. 21, 2000

Related U.S. Application Data

(60) Provisional application No. 60/139,124, filed on Jun. 14, 1999.

(51) Int. Cl.
*A61N 7/00* (2006.01)
(52) U.S. Cl. .............................. 601/2; 604/22; 424/9.52
(58) Field of Classification Search ................. 600/458, 600/437, 439; 601/2–4; 604/22; 424/9.5–9.52
See application file for complete search history.

(56) References Cited

U.S. PATENT DOCUMENTS

| 1,053,782 A | 6/1913 | Dickey et al. |
| 1,604,870 A | 10/1926 | Asman |
| 2,914,829 A | 12/1959 | Willemain |

(Continued)

FOREIGN PATENT DOCUMENTS

AU   199950292745022   2/2000

(Continued)

OTHER PUBLICATIONS

Abstract, (Proceedings of the 11th Int'l, Conference on Medical and Biological Engineering) "Ultrasonic Stimulation of Fracture Healing", 1976.

(Continued)

*Primary Examiner*—Ruth S Smith
(74) *Attorney, Agent, or Firm*—Kilpatrick Stockton LLP

(57) ABSTRACT

A method and kit for therapeutically treating bone and tissue injuries using ultrasound. The method includes the steps of introducing an ultrasound contrast agent into the patient, preferably, the patient's blood stream, and impinging ultrasonic waves in proximity to an injury. The ultrasound contrast agent facilitate in lowering the cavitation threshold, i.e., the energy required for the cavitation, to a level attainable by the ultrasonic waves to induce acoustic intracellular microstreaming to accelerate the healing process. The method further includes the steps of maintaining the resonance bubble frequency of the microbubbles of the ultrasound contrast agent from 0.5 MHz to 10 MHz; maintaining the acoustic transmit frequency of the ultrasound waves from 10 kHz to 10 MHz; and maintaining the acoustic spatial average-temporal average (SATA) intensity of the ultrasonic waves from 5 to 500 mW/cm$^2$. The kit of the invention includes at least one ergonomically constructed ultrasonic transducer (16) configured to cooperate with a placement module (14) for placement in proximity to an injury and a portable, ergonomically constructed main operating unit (12) constructed to fit within a pouch (18) worn by the patient.

12 Claims, 5 Drawing Sheets

U.S. PATENT DOCUMENTS

| | | |
|---|---|---|
| 2,920,853 A | 1/1960 | Bufogle |
| 3,117,571 A | 1/1964 | Fry et al. |
| 3,134,451 A | 5/1964 | Hanssen |
| 3,193,034 A | 7/1965 | Hutchinson et al. |
| 3,241,375 A | 3/1966 | Canzonen |
| 3,304,036 A | 2/1967 | Davis |
| 3,310,049 A | 3/1967 | Clynes |
| 3,433,663 A | 3/1969 | Underwood |
| 3,499,437 A | 3/1970 | Balamuth |
| 3,521,225 A | 7/1970 | Kursman et al. |
| 3,550,586 A | 12/1970 | Balamuth |
| 3,575,050 A | 4/1971 | Lynnworth |
| 3,594,993 A | 7/1971 | Heyse |
| 3,664,626 A | 5/1972 | Sneller |
| 3,701,352 A | 10/1972 | Bosworth |
| 3,714,619 A | 1/1973 | Morgan et al. |
| 3,729,162 A | 4/1973 | Salvato |
| 3,760,799 A | 9/1973 | Crowson |
| 3,767,195 A | 10/1973 | Dimick |
| 3,828,769 A | 8/1974 | Mettler |
| 3,855,638 A | 12/1974 | Pilliar |
| 3,890,953 A | 6/1975 | Kraus et al. |
| 3,961,380 A | 6/1976 | Garr |
| 3,986,212 A | 10/1976 | Sauer |
| 4,037,592 A | 7/1977 | Kronner |
| 4,105,017 A | 8/1978 | Ryaby et al. |
| 4,108,165 A | 8/1978 | Kopp et al. |
| 4,127,125 A | 11/1978 | Takemoto et al. |
| 4,141,524 A | 2/1979 | Corvese, Jr. |
| 4,164,794 A | 8/1979 | Spector et al. |
| 4,170,045 A | 10/1979 | Estes |
| 4,176,664 A | 12/1979 | Talish |
| 4,195,517 A | 4/1980 | Kalinoski et al. |
| 4,206,516 A | 6/1980 | Pilliar |
| 4,216,766 A | 8/1980 | Duykers et al. |
| 4,227,111 A | 10/1980 | Cross et al. |
| 4,229,992 A | 10/1980 | McKee et al. |
| 4,233,477 A | 11/1980 | Rice et al. |
| 4,266,532 A | 5/1981 | Ryaby et al. |
| 4,266,533 A | 5/1981 | Ryaby et al. |
| 4,269,797 A | 5/1981 | Mikiya et al. |
| 4,291,025 A | 9/1981 | Pellico |
| 4,296,753 A | 10/1981 | Goudin |
| 4,312,536 A | 1/1982 | Lloyd |
| 4,315,503 A | 2/1982 | Ryaby et al. |
| 4,315,514 A | 2/1982 | Drewes et al. |
| 4,347,645 A | 9/1982 | Iseki |
| 4,351,069 A | 9/1982 | Ballintyn et al. |
| 4,355,428 A | 10/1982 | Deloison et al. |
| 4,358,105 A | 11/1982 | Sweeney, Jr. |
| 4,361,154 A | 11/1982 | Pratt, Jr. |
| 4,365,359 A | 12/1982 | Raab |
| 4,383,533 A | 5/1983 | Bhagat et al. |
| 4,407,044 A | 10/1983 | Iseki |
| 4,410,158 A | 10/1983 | Maffei |
| 4,421,119 A | 12/1983 | Pratt, Jr. |
| 4,431,038 A | 2/1984 | Rome |
| 4,440,025 A | 4/1984 | Hayakawa et al. |
| 4,441,486 A | 4/1984 | Pounds |
| 4,446,586 A | 5/1984 | Reed et al. |
| 4,452,326 A | 6/1984 | Hanssen et al. |
| 4,467,659 A | 8/1984 | Baumoel |
| 4,476,874 A | 10/1984 | Taenzer et al. |
| 4,482,942 A | 11/1984 | Blaisdell et al. |
| 4,511,921 A | 4/1985 | Harlan et al. |
| 4,530,360 A | 7/1985 | Duarte |
| 4,536,894 A | 8/1985 | Galante et al. |
| 4,542,539 A | 9/1985 | Rowe, Jr. et al. |
| 4,542,744 A | 9/1985 | Barnes et al. |
| 4,550,714 A | 11/1985 | Talish |
| 4,556,066 A | 12/1985 | Semrow |
| 4,557,148 A | 12/1985 | Akiyama |
| 4,570,487 A | 2/1986 | Gruber |
| 4,570,640 A | 2/1986 | Barsa |
| 4,570,927 A | 2/1986 | Petrofsky et al. |
| 4,573,996 A | 3/1986 | Kwiatek et al. |
| 4,594,662 A | 6/1986 | Devaney |
| 4,612,160 A | 9/1986 | Donlevy et al. |
| 4,627,429 A | 12/1986 | Tsuk |
| 4,630,323 A | 12/1986 | Sage et al. |
| 4,644,942 A | 2/1987 | Sump |
| 4,646,725 A | 3/1987 | Moasser |
| 4,657,543 A | 4/1987 | Langer et al. |
| 4,669,483 A | 6/1987 | Hepp et al. |
| 4,677,438 A | 6/1987 | Michiguchi et al. |
| 4,680,967 A | 7/1987 | Rost |
| 4,687,195 A | 8/1987 | Potts |
| 4,689,986 A | 9/1987 | Carson et al. |
| 4,708,127 A | 11/1987 | Abdelghani |
| 4,710,655 A | 12/1987 | Masaki |
| 4,725,272 A | 2/1988 | Gale |
| 4,726,099 A | 2/1988 | Card et al. |
| 4,763,661 A | 8/1988 | Sommer et al. |
| 4,770,184 A | 9/1988 | Greene, Jr. et al. |
| 4,774,959 A | 10/1988 | Palmer et al. |
| RE32,782 E | 11/1988 | Pratt, Jr. |
| 4,782,822 A | 11/1988 | Ricken |
| 4,787,070 A | 11/1988 | Suzuki et al. |
| 4,787,888 A | 11/1988 | Fox |
| 4,792,336 A | 12/1988 | Hlavacek et al. |
| 4,802,477 A | 2/1989 | Gabbay |
| 4,830,015 A | 5/1989 | Okazaki |
| 4,836,316 A | 6/1989 | Carnevale et al. |
| 4,855,911 A | 8/1989 | Lele et al. |
| 4,858,599 A | 8/1989 | Halpern |
| 4,867,169 A | 9/1989 | Machida et al. |
| 4,891,849 A | 1/1990 | Robinson |
| 4,905,671 A | 3/1990 | Senge et al. |
| 4,913,157 A | 4/1990 | Pratt, Jr. et al. |
| 4,917,092 A | 4/1990 | Todd et al. |
| 4,917,376 A | 4/1990 | Lo |
| 4,920,966 A | 5/1990 | Hon et al. |
| 4,926,870 A | 5/1990 | Brandenburger |
| 4,928,959 A | 5/1990 | Bassett et al. |
| 4,930,358 A | 6/1990 | Motegi et al. |
| 4,932,951 A | 6/1990 | Liboff et al. |
| 4,933,230 A | 6/1990 | Card et al. |
| 4,936,303 A | 6/1990 | Detwiler et al. |
| 4,941,474 A | 7/1990 | Pratt, Jr. |
| 4,947,853 A | 8/1990 | Hon |
| 4,979,501 A | 12/1990 | Valchanov et al. |
| 4,982,730 A | 1/1991 | Lewis, Jr. |
| 4,984,462 A | 1/1991 | Hass, Jr. et al. |
| 4,986,275 A | 1/1991 | Ishida et al. |
| 4,993,413 A | 2/1991 | McLeod et al. |
| 4,995,883 A | 2/1991 | Demane et al. |
| 5,000,183 A | 3/1991 | Bonnefous |
| 5,000,442 A | 3/1991 | Dalebout et al. |
| 5,003,965 A | 4/1991 | Talish et al. |
| 5,004,476 A | 4/1991 | Cook |
| 5,016,641 A | 5/1991 | Schwartz |
| 5,018,285 A | 5/1991 | Zolman et al. |
| 5,046,484 A | 9/1991 | Bassett et al. |
| 5,054,490 A | 10/1991 | Rossman et al. |
| 5,067,940 A | 11/1991 | Liboff et al. |
| 5,080,672 A | 1/1992 | Bellis |
| 5,088,976 A | 2/1992 | Liboff et al. |
| 5,099,702 A | 3/1992 | French |
| 5,100,373 A | 3/1992 | Liboff et al. |
| 5,103,806 A | 4/1992 | McLeod et al. |
| 5,106,361 A | 4/1992 | Liboff et al. |
| 5,107,853 A | 4/1992 | Plyter |
| 5,108,452 A | 4/1992 | DeMane et al. |
| 5,133,420 A | 7/1992 | Smith |

| | | | | | | |
|---|---|---|---|---|---|---|
| 5,134,999 A | 8/1992 | Osipov | 5,466,215 A | 11/1995 | Lair et al. | |
| 5,139,498 A | 8/1992 | Astudillo Ley | 5,468,220 A | 11/1995 | Sucher | |
| 5,140,988 A | 8/1992 | Stouffer et al. | 5,476,438 A | 12/1995 | Edrich et al. | |
| 5,143,069 A | 9/1992 | Kwon et al. | 5,478,306 A | 12/1995 | Stoner | |
| 5,143,073 A | 9/1992 | Dory | 5,484,388 A | 1/1996 | Bassett et al. | |
| 5,154,189 A | 10/1992 | Oberlander | 5,492,525 A | 2/1996 | Gibney | |
| 5,163,598 A | 11/1992 | Peters et al. | 5,495,846 A | 3/1996 | Uehara et al. | |
| 5,172,692 A | 12/1992 | Kulow et al. | 5,496,256 A | 3/1996 | Bock et al. | |
| 5,178,134 A | 1/1993 | Vago | 5,501,657 A | 3/1996 | Feero | |
| 5,181,512 A | 1/1993 | Viebach et al. | 5,507,800 A | 4/1996 | Strickland | |
| 5,184,605 A | 2/1993 | Grzeszykowski | 5,507,830 A | 4/1996 | DeMane et al. | |
| 5,186,162 A | 2/1993 | Talish et al. | 5,509,933 A | 4/1996 | Davidson et al. | |
| 5,191,880 A | 3/1993 | McLeod et al. | 5,520,612 A | 5/1996 | Winder et al. | |
| 5,197,475 A | 3/1993 | Antich et al. | 5,524,624 A | 6/1996 | Tepper et al. | |
| 5,201,766 A | 4/1993 | Georgette | 5,526,815 A | 6/1996 | Granz et al. | |
| 5,209,221 A | 5/1993 | Riedlinger | 5,541,489 A | 7/1996 | Dunstan | |
| 5,211,160 A | 5/1993 | Talish et al. | 5,547,459 A | 8/1996 | Kaufman et al. | |
| 5,230,334 A | 7/1993 | Klopotek | 5,556,372 A | 9/1996 | Talish et al. | |
| 5,230,345 A | 7/1993 | Curran et al. | 5,578,060 A | 11/1996 | Pohl et al. | |
| 5,230,646 A | 7/1993 | Thorup | 5,615,466 A | 4/1997 | Safari et al. | |
| 5,230,921 A | 7/1993 | Waltonen et al. | 5,626,554 A | 5/1997 | Ryaby et al. | |
| 5,235,981 A | 8/1993 | Hascoet et al. | 5,626,630 A | 5/1997 | Markowitz et al. | |
| 5,254,123 A | 10/1993 | Bushey | 5,630,837 A | 5/1997 | Crowley | |
| 5,259,384 A | 11/1993 | Kaufman et al. | D380,440 S | 7/1997 | Talish et al. | |
| 5,269,306 A | 12/1993 | Warnking et al. | 5,644,093 A | 7/1997 | Wright et al. | |
| 5,273,028 A | 12/1993 | McLeod et al. | 5,648,941 A | 7/1997 | King | |
| 5,280,728 A | 1/1994 | Sato et al. | 5,656,016 A | 8/1997 | Ogden | |
| 5,284,143 A | 2/1994 | Rattner | 5,665,141 A * | 9/1997 | Vago | 95/30 |
| 5,285,788 A | 2/1994 | Arenson et al. | 5,680,863 A | 10/1997 | Hossack et al. | |
| 5,295,931 A | 3/1994 | Dreibelbis et al. | 5,690,608 A | 11/1997 | Watanabe et al. | |
| 5,301,683 A | 4/1994 | Durkan | 5,691,960 A | 11/1997 | Gentilman et al. | |
| 5,307,284 A | 4/1994 | Brunfeldt et al. | 5,699,803 A | 12/1997 | Carodiskey | |
| 5,309,898 A | 5/1994 | Kaufman et al. | 5,702,353 A | 12/1997 | Guzzini et al. | |
| 5,310,408 A | 5/1994 | Schryver et al. | 5,702,389 A | 12/1997 | Taylor et al. | |
| 5,314,401 A | 5/1994 | Tepper | 5,706,818 A | 1/1998 | Gondo | |
| 5,316,000 A | 5/1994 | Chapelon et al. | 5,708,236 A | 1/1998 | Shaanan et al. | |
| 5,318,561 A | 6/1994 | McLeod et al. | 5,721,400 A | 2/1998 | Haraldsson et al. | |
| 5,318,779 A | 6/1994 | Hakamatsuka et al. | 5,725,482 A | 3/1998 | Bishop | |
| 5,322,067 A | 6/1994 | Prater et al. | 5,728,095 A | 3/1998 | Taylor et al. | |
| 5,323,769 A | 6/1994 | Bommannan et al. | 5,730,705 A | 3/1998 | Talish et al. | |
| 5,327,890 A | 7/1994 | Matura et al. | 5,738,625 A | 4/1998 | Gluck | |
| 5,330,481 A | 7/1994 | Hood et al. | 5,741,317 A | 4/1998 | Ostrow | |
| 5,330,489 A | 7/1994 | Green et al. | 5,743,862 A | 4/1998 | Izumi | |
| 5,334,214 A | 8/1994 | Putnam | 5,755,746 A | 5/1998 | Lifshey et al. | |
| 5,339,804 A | 8/1994 | Kemp | 5,762,616 A | 6/1998 | Talish | |
| 5,340,510 A | 8/1994 | Bowen | 5,779,600 A | 7/1998 | Pape | |
| 5,351,389 A | 10/1994 | Erickson et al. | 5,785,656 A | 7/1998 | Chiabrera et al. | |
| 5,363,850 A | 11/1994 | Soni et al. | 5,818,149 A | 10/1998 | Safari et al. | |
| 5,366,465 A | 11/1994 | Mirza | 5,829,437 A | 11/1998 | Bridges | |
| 5,367,500 A | 11/1994 | Ng | 5,843,741 A | 12/1998 | Wong et al. | |
| 5,368,044 A | 11/1994 | Cain et al. | 5,856,622 A | 1/1999 | Yamamoto et al. | |
| 5,376,065 A | 12/1994 | McLeod et al. | 5,868,649 A | 2/1999 | Erickson et al. | |
| 5,380,269 A | 1/1995 | Urso | 5,871,446 A | 2/1999 | Wilk | |
| 5,386,830 A | 2/1995 | Powers et al. | 5,886,302 A | 3/1999 | Germanton et al. | |
| 5,393,296 A | 2/1995 | Rattner | 5,891,143 A | 4/1999 | Taylor et al. | |
| 5,394,877 A | 3/1995 | Orr et al. | 5,899,425 A | 5/1999 | Corey Jr. et al. | |
| 5,394,878 A | 3/1995 | Frazin et al. | 5,904,659 A | 5/1999 | Duarte et al. | |
| 5,398,290 A | 3/1995 | Brethour | 5,906,580 A | 5/1999 | Kline et al. | |
| 5,400,795 A | 3/1995 | Murphy et al. | 5,954,675 A | 9/1999 | Dellagatta | |
| 5,405,389 A | 4/1995 | Conta et al. | 5,957,814 A | 9/1999 | Eschenbach | |
| 5,409,446 A | 4/1995 | Rattner | 5,962,790 A | 10/1999 | Lynnworth et al. | |
| RE34,959 E | 5/1995 | Potts | 5,971,984 A | 10/1999 | Taylor et al. | |
| 5,413,550 A | 5/1995 | Castel | 5,997,490 A | 12/1999 | McLeod et al. | |
| 5,415,167 A | 5/1995 | Wilk | 6,019,710 A | 2/2000 | Dalebout et al. | |
| 5,417,215 A | 5/1995 | Evans et al. | 6,022,349 A | 2/2000 | McLeod et al. | |
| 5,424,550 A | 6/1995 | Kawano et al. | 6,028,066 A | 2/2000 | Unger | |
| 5,425,954 A | 6/1995 | Thompson et al. | 6,030,386 A | 2/2000 | Taylor et al. | |
| 5,431,612 A | 7/1995 | Holden | 6,048,323 A | 4/2000 | Hon | |
| 5,434,827 A | 7/1995 | Bolorforosh | 6,050,943 A | 4/2000 | Slayton et al. | |
| 5,441,051 A | 8/1995 | Hileman et al. | 6,061,597 A | 5/2000 | Rieman et al. | |
| 5,441,058 A | 8/1995 | Fareed | 6,065,350 A | 5/2000 | Hill et al. | |
| 5,448,994 A | 9/1995 | Iinuma | 6,068,596 A | 5/2000 | Weth et al. | |
| 5,460,595 A | 10/1995 | Hall et al. | 6,080,088 A | 6/2000 | Petersen et al. | |

| | | | |
|---|---|---|---|
| 6,082,181 A | 7/2000 | Greenwood | |
| 6,086,078 A | 7/2000 | Ferez | |
| 6,088,613 A * | 7/2000 | Unger | 600/420 |
| 6,093,135 A | 7/2000 | Huang | |
| 6,105,431 A | 8/2000 | Duffill et al. | |
| 6,165,144 A | 12/2000 | Talish et al. | |
| 6,179,797 B1 | 1/2001 | Brotz | |
| 6,190,336 B1 | 2/2001 | Duarte et al. | |
| 6,206,843 B1 | 3/2001 | Iger et al. | |
| 6,213,958 B1 | 4/2001 | Winder | |
| 6,234,975 B1 | 5/2001 | McLeod et al. | |
| 6,234,990 B1 | 5/2001 | Rowe et al. | |
| 6,258,020 B1 | 7/2001 | Lopez | |
| 6,261,221 B1 | 7/2001 | Tepper et al. | |
| 6,261,249 B1 | 7/2001 | Talish et al. | |
| 6,264,650 B1 | 7/2001 | Hovda et al. | |
| 6,273,864 B1 | 8/2001 | Duarte et al. | |
| 6,311,402 B1 | 11/2001 | Brandl et al. | |
| 6,322,527 B1 | 11/2001 | Talish | |
| 6,355,006 B1 | 3/2002 | Ryaby et al. | |
| 6,360,027 B1 | 3/2002 | Hossack et al. | |
| 6,394,955 B1 | 5/2002 | Perlitz | |
| 6,397,683 B1 | 6/2002 | Hagenmeyer et al. | |
| 6,406,443 B1 | 6/2002 | Talish | |
| 6,436,060 B1 | 8/2002 | Talish | |
| 6,443,898 B1 * | 9/2002 | Unger et al. | 600/458 |
| 6,464,687 B1 * | 10/2002 | Ishikawa et al. | 604/891.1 |
| 6,503,214 B1 | 1/2003 | Talish | |
| 6,524,261 B2 | 2/2003 | Talish et al. | |
| 6,685,656 B1 | 2/2004 | Duarte et al. | |
| 6,733,468 B2 | 5/2004 | Talish | |
| 6,932,308 B2 | 8/2005 | Talish et al. | |
| 6,960,173 B2 | 11/2005 | Babaev | |
| 2002/0016557 A1 | 2/2002 | Duarte | |
| 2002/0068871 A1 | 6/2002 | Mendlein et al. | |
| 2002/0103448 A1 | 8/2002 | Babaev | |
| 2002/0115960 A1 | 8/2002 | Redding, Jr. | |
| 2002/0156400 A1 | 10/2002 | Babaev | |
| 2002/0190136 A1 | 12/2002 | Babaev | |
| 2003/0013956 A1 | 1/2003 | Michaeli | |
| 2003/0153848 A1 | 8/2003 | Talish | |
| 2003/0153849 A1 | 8/2003 | Huckle | |
| 2004/0127790 A1 * | 7/2004 | Lang et al. | 600/438 |
| 2005/0096548 A1 | 5/2005 | Talish | |
| 2006/0106424 A1 | 5/2006 | Bachem | |

FOREIGN PATENT DOCUMENTS

| | | |
|---|---|---|
| CA | 1328485 | 4/1994 |
| DE | 3639263 A1 | 6/1987 |
| DE | 19613425 | 1/1997 |
| DE | 298 11 185 U1 | 10/1998 |
| DE | 41 11 055 A1 | 10/2001 |
| EP | 0 181 506 A2 | 5/1986 |
| EP | 331 348 A1 | 9/1989 |
| EP | 0 425 765 A1 | 5/1991 |
| EP | 0 536 875 A1 | 4/1993 |
| EP | 0 679 371 A1 | 11/1995 |
| EP | 0 695 559 | 2/1996 |
| GB | 2156983 A | 10/1985 |
| GB | 2277448 A | 11/1994 |
| GB | 2 303 552 A | 2/1997 |
| JP | 62-47359 | 3/1987 |
| JP | 4-82567 | 3/1992 |
| JP | 4-82568 | 3/1992 |
| JP | 4-82569 | 3/1992 |
| JP | 5-269159 | 10/1993 |
| WO | WO 85/03449 | 8/1985 |
| WO | WO 88/00845 | 2/1988 |
| WO | WO 88/02250 | 4/1988 |
| WO | WO 90/06720 | 6/1990 |
| WO | WO 94/13411 | 6/1994 |
| WO | WO 95/03744 | 2/1995 |
| WO | WO 95/33416 | 12/1995 |
| WO | WO 96/25112 | 8/1996 |
| WO | WO 96/25888 | 8/1996 |
| WO | WO 97/33649 | 9/1997 |
| WO | WO 98/10729 | 3/1998 |
| WO | WO 98/29036 | 7/1998 |
| WO | WO 98/34578 | 8/1998 |
| WO | WO 98/47570 | 10/1998 |
| WO | WO 99/18876 | 4/1999 |
| WO | WO 99/22652 | 5/1999 |
| WO | WO 99/48621 | 9/1999 |
| WO | WO 99/56829 | 11/1999 |
| WO | WO 00/03663 | 1/2000 |
| WO | WO 00/28925 | 5/2000 |
| WO | WO 00/67846 | 11/2000 |
| WO | WO 00/71207 | 11/2000 |
| WO | WO 00/76406 A1 | 12/2000 |

OTHER PUBLICATIONS

Abstract, (Proceedings of the III Congress on Biomedical Engineering) "Ultrasonic Action on Callus Formation in Bones", 1975.

Abstract, (Proceedings of the IV Brazilain Congress on Biomedical Engineering) "Ultrasound in the Treatment of Fractures", 1977.

ASTM Designation: D790M-93 Metric, "Standard Test Methods for flexural Properties of Unreinforced and Reinforced Plastics and Electrical Insulating Materials (Metric)", pp. 176-184, (Dec. 1993).

ASTM Designation: C1161-90, "Standard Test Method for Flexural Strength of Advanced Ceramics at Ambient Temperature," pp. 324-330.(Feb. 1991).

Arai et al., "The Effect of Ultrasound Stimulation on Disuse Osteoporosis", Brags 17, 1993.

Berridge, M.J., "Inositol Trisphosphate and Calcium Signaling", *Nature* (1993), 361: 315-325.

Clarke, P.R. et al., "Physical and Chemical Aspects of Ultrasonic Disruption of Cells", *JASA* (1969), 47(2): 649-653.

Duarte, L.R., "The Stimulation of Bone Growth by Ultrasound", *Arch. Orthop. Trauma Surg* (1983), 101: 153-159.

Dyson, M., "Therapeutic Applications of Ultrasound", *Biological Effects of Ultrasound* (1985), Nyborg, W.L. and Ziskin, M.C., eds; Churchill Livingstone Inc., New York, Chapter 11.

Goodship, A.E. et al., "The Influence of Induced Micromovement Upon the Healing of Experimental Tibial Fractures", *J. Bone and Joint Surg.* (1985), 67-B(4): 650-655.

Heckman, J.D. et al., "Acceleration of Tibial Fracture Healing by Non-Invasive Low Intensity Pulsed Ultrasound", *J. Bone and Joint Surg:* (1994), 76-A(1): 26-34.

Hill, C.R., "Ultrasonic Exposure Thresholds for Changes in Cells and Tissues", *JASA* (1972), 52(2): 667-672.

Howkins, S.D., "Diffusion Rates and the Effect of Ultrasound", *Ultrasonics* (1969), 129-130.

Kristiansen, T.K. et al., "Accerlated Healing of Distal Radial Fractures with the Use of Specific, Low-Intensity Ultrasound", *J. Bone and Joint Surg.* (1997), 79-A(7) 961-973.

Maurice Hilario, "Low-Intensity Ultrasound Radiation in the Tissue Repair of Trophic Leg Ulcers", 1983, University of Sao Paulo, pp. 1-125.

Phoenix (Business Wire), Jul. 8, 1997 via CompanyLink - OrthoLogic Corp.

"Reflex Sympathetic Dystrophy, Does RSD Exist?" www.arbon.com (Jun. 4, 1997).

"Reflex Sympathetic Dystrophy: The Pain That Doesn't Stop," tcc.cc.nc.us (Jun. 4, 1997).

RSDnet.org "Reflex Sympathetic Dystrophy," www.rsdnet.org (Jun. 4, 1997).

RSDnet.org "Reflex Sympathetic Dystrophy," www.rsdnet.org (Jun. 4, 1997).

Ter Haar, G., et al., "Basic Physics of Therapeutic Ultrasound", *Physiotherapy* (1987), 73(3): 110-113.

Wallace, A.L.; Draper E.R.C.; Strachan, R.K.; McCarthy, I.D.; Hughes, S.P.F., "The Vascular Response to Fracture Micromovement", *Clinical Orthopaedics and Related Research* (1994), 301: 281-290.

Wang, S.J. et al., "Low-Intensity Ultrasound Treatment Increases Strength in a Rat Femoral Fracture Model", *J. Ortho Rsearch* (1994), 12: 40-47.

Webster, D.F. et al., "The Role of Ultrasound-Induced Cavitation in the 'In Vitro' Stimulation of Collagen Synthesis in Human Fibroblasts", *Ultrasonics* (1980), 33-37.

Yang, K.H. et al., "Exposure to Low-Intensity Ultrasound Treatment Increases Aggrecan Gene Expression in a RatFemur Fracture Model", *J. Ortho Research* (1996), 14:802-809.

Treatment of Osteochondral Defects in Rabbits with SAFHS - Part III, EX1097-01R (Aug. 26, 1997).

Cook, Stephen and L. Patron, "Treatment of Osteochondral Defects in Rabbits with SAFHS - A Mosalcplasty Model" —Final Report, EX1098-04R (Aug. 12, 1999).

Acoustic Emission - An Update, by Arthur E. Lord, Jr., 1981, Physical Acoustics, vol. XV, pp. 295-360.

Acoustic Emission and Diagnostic of Osteoporosis, by S. Hanagud, G. T. Hannon and R. Clinton, 1974, Ultrasonic Symposium Proceedings (IEEE), pp. 77-81.

Acoustic Emission In Bone Substance, by S. Hanagud, R.G. Clinton and J.P. Lopez, 1973, Biomechanics Symposium Proceedings (ASME), pp. 79-81.

Acoustic Emission Inspection, by Adrian A. Pollack, 1992, ASM Handbook, vol. 17, Nondestructive Evaluation and Quality Control, pp. 278-293.

Acoustic Emission Techniques in the Development of a Diagnostic Tool for Osteoporosis, by S. Hanagud and R. G. Clinton, 1975, Ultrasonic Symposium Proceedings (IEEE), pp. 41-45.

Application of an intelligent signal processing system to acoustic emission analysis, by Igo Grabec and Wolfgang Sachse, Mar. 1989, Acoustic Society of America, pp. 787-791.

Application of correlation techniques for localization of acoustic emission sources, by I. Grabec, 1978, IPC Business Press Ltd., pp. 111-115.

Comejo, et al., "Large-Area Flexible-Array Piezoelectric Ceramic/Polymer composite Transducer for Bone Healing Acceleration," presented at ISAFXI, Montreux, Switzerland (1998).

Fritton, et al., "Whole-Body Vibration in the Skeleton: Development of a Resonance-Based Testing Device," *Annals of Biomedical Engineering*, vol. 25, pp. 831-839 (1997).

Goodship, et al., "Low magnitude high frequency mechanical stimulation of endochondral bone repair" 43 rd Annual Meeting Orthopeadic Research Society, vol. 22, Sec. 1, Feb. 9-13 (1997).

J. Kenwright, et al., "Controlled Mechanical Stimulation in the Treatment of Fibial Fractures," Orthopedics, Clinical Orthopedics and Related Research (1989) 241:36-47.

Jankovich, "The Effects of Mechanical Vibration on Bone Development in the Rat," *J. Biomechanics*, 1972, vol. 5, pp. 241-250.

Ko, "Preform Fiber Architecture for Ceramic-Matrix Composites," Ceramic Bullentin, vol. 68, No. 2, pp. 401-414 (1989).

McLeod, et al., "Improved Postural Stability Following Short Term Exposure to Low Level Whole Body Vibration," 44th Annual Meeting, Orthopaedic Research Society, Mar. 16-19, 1998, New Orleans, Louisiana, p. 89-15.

Newnham, et al., Connectivity and Piezoelectric-Pyroelectric Composites, Med. Res. Bull., vol. 13, pp. 525-536 (1978).

Pilgrim, et al., "An Extension of the Composite Nomenclature Scheme," Med. Res. Bull., vol. 22, pp. 877-894 (1987).

Powell, et al., "A Performance Appraisal of Flexible Array Structures Using a Facet Ensemble Scattering Technique," *1991 Ultrasonic Symposium*, pp. 753-766.

Powell, et al., Flexible Ultrasonic Transducer Arrays for Nondestructive Evaluation Applications - Part I: The Theoretical Modeling Approach, "*IEEE Transactions on Ultrasonics, Ferroelectrics, and Frequency Control*," vol. 43, No. 3, May 1996, pp. 385-392.

Powell, et al., "Flexible Ultrasonic Transducer Arrays for Nondestructive Evaluation Applications - Part II: Performance Assessment of different Array Configurations," *IEEE Transactions on Ultrasonics, Ferroelectrics, and Frequency Control*, vol. 43, May 1996, pp. 393-402.

Sarvazyan, "Some General Problems of Biological Action of Ultrasound," IEEE Transactions on Sonics and Ultrasonics, vol. 30, No. 1, Jan. 1983.

Ultrasound as a Tool for Investigation Bone: Fundamental Principles and Perspectives for Use in Osteoporosis, by J. G. Bloch, 1993, Expansion Scientifique Francaise.

Y. Qin, et al., "Correlation of In Vivo Bone Adaption and Mechanical Parameters Using Low Magnitude, High Frequency Loading," 41st Annual Meeting Orthopaedic Research Soc., vol. 20 - Sec. 1, Feb. 13-16 (1995).

Cass, "Fabrication of Continuous Ceramic Fiber by the Viscous Suspension Spinning Process," *Ceramic Bullentin*, vol. 70, No. 3, pp. 424-429 (1991).

"Development of Flexible Pieoelectric Transducers and Matching Layers for EXOGEN Incorporated," Final Report, Covering Period Apr. 1, 1997 to Feb. 28, 1998, Rutgers University.

Grewe, et al., "Acoustic Properties of Particle Polymer Composite for Ultrasonic Transducer backing Applications," *IEEE*, (1990).

Grewe, Martha G., "Acoustic Matching And Backing Layer for Medical Ultrasonic Transducers," A Thesis in Solid State Science, The Pennsylvania State University; (May 1989), The Center for Ceramics Research, Rutgers.

Gururaja, T., "Piezoelectric Composite Materials for Ultrasonic Transducer Applications," A Thesis in Solid State Science, The Pennsylvania State University, May 1984.

Gururaja, "Piezoelectrics for Medical Ultrasonic Imaging," *Am. Ceram. Soc. Bull.*, vol. 73, No. 5, pp. 50-55 (May 1994).

Hall, et al., "The design and evaluation of ultrasonic arrays using 1-3 connectivity composites," *SPIE*, pp. 216-227, vol. 1733 (1992).

Niemczewski, B., "A Comparison of Ultrasonic Cavitation Intensity in Liquids," *Ultrasonics*, vol. 18, pp. 107-110, 1980.

Pilla, et al., "Non-Invasive Low-Intensity Pulsed Ultrasound Accelerates Bone Healing in the Rabbit," *Journal of Orthopaedic Trauma*, vol. 4, No. 3, pp. 246-253 (1990).

Safari, "Development of piezoelectric composites for transducers," *J. Phys.France*, 4:1129-1149 (1994).

Selfridge, "Approximate Material Properties in Isotropic Materials," *IEEE Transactions on Sonics and Ultrasonics*, May 9, 1985).

Souquet, et al., "Design of Low-Loss Wide-Band Ultrasonic Transducers for Noninvasive Medical Application," *IEEE Transactions on Sonics and Ultrasonics*, pp. 75-81, vol. SU-26, No. 2, Mar. 1979.

Waller, et al., "Poling of Lead Zirconate Titanate Ceramics and Flexible Piezoelectric Composites by the Corona Discharge Technique," *J. Am. Ceram. Soc.*, 72(2):322-24 (1989).

Winder, Alan, "Synthetic Structural Imaging and Volume Estimation of Biological Tissue Organs," Acoustic Sciences Associates. Dec. 1995.

Winder, Alan, "Acoustic Emission Monitoring for the Detection, Localization and Classification of Metabolic Bone Disease," Acoustic Sciences Associates, Dec. 1995.

Wu and Cubberly, "Measurement of Velocity and Attenuation of Shear Waves in Bovine Compact Bone Using Ultrasonic Spectroscopy," Med. & Biol., vol. 23, No. 1, 129-134, 1997.

Pethica, B.A., et al. The Dose-Response Relationship in PEMP Therapy of Ununited Fractures, *Transactions of the 8[th]Annual Meeting of the Bioelectrical Repair and Growth Society(BRAGS)*, Washington, D.C. (Jun. 1988) Abstarct, one page.

Tavakoll and Evans, "The Effect of Bone Structure on Ultrasonic Attenuation and Velocity," *Ultrasonics*, vol. 30, No. 6, pp. 389-395 (1992).

Brochure: "The Science Behind the Technology," distributed by Smith & Nephew for EXOGEN. (undated).

Treatment of Osteochondral Defects in Rabbits with SAFHS - Parts I and II, EX1095-01R, EX1096-01R (undated).

Clough, R. and J. Simmons, "Theory of Acoustics Emission," Metallurgy Division, national Bureau of Standards. (undated).

Pauer, "Flexible Piezoelectric Material," pp. 1-5, (undated).

Bascom, "Other Continuous Fibers," 118/Constitutent Material Form (undated).

Bascom, "Other Discontinuous Forms," 120/Constituent Material Forms (undated).

\* cited by examiner

METHOD FOR CAVITATION-INDUCED TISSUE HEALING WITH LOW INTENSITY ULTRASOUND

PRIORITY

This application is the U.S. national phase of International Application No. PCT/US00/16471 filed on 14 Jun. 2000 which claims priority to U.S. Provisional Application No. 60/139,124 filed on 14 Jun. 1999 by Alan A. Winder and Roger J. Talish, the contents of which are incorporated herein by reference.

BACKGROUND OF THE INVENTION

1. Field of the Invention

The present invention relates to a method and kit for therapeutically treating injuries by inducing acoustic intracellular microstreaming by using low intensity ultrasound. More particularly, the present invention relates to a method and kit which utilizes an ultrasound contrast agent and an ergonomically constructed ultrasonic transducer for placement in proximity to an injury for therapeutically treating the injury by producing acoustic cavitation at the trauma site. The ultrasound contrast agent is introduced into the patient, preferably, the patient's blood stream, prior to emitting ultrasonic waves toward the trauma site to lower the cavitation threshold, i.e., the energy required for cavitation, to a level attainable with low intensity ultrasound.

2. Description of the Related Art

The use of ultrasound or acoustic energy to therapeutically treat and evaluate bone and tissue injuries is known. Impinging ultrasonic pulses having appropriate parameters, e.g., frequency, pulse repetition, and amplitude, for suitable periods of time and at a proper external location adjacent to a bone or tissue injury has been determined to accelerate the natural healing of, for example, bone breaks and fractures.

U.S. Pat. No. 4,530,360 to Duarte describes a basic non-invasive therapeutic technique and apparatus for applying ultrasonic pulses from an operative surface placed on the skin at a location adjacent a bone injury. The applicator described in the Duarte patent has a plastic tube which serves a grip for the operator, an RF plug attached to the plastic tube for connection to an RF source, and internal cabling connected to an ultrasonic transducer. To apply the ultrasound pulses during treatment an operator must manually hold the applicator in place until the treatment is complete. As a result, the patient is, in effect, immobilized during treatment. The longer the treatment period, the more the patient is inconvenienced. The Duarte patent as well as U.S. Pat. No. 5,520,612 to Winder et al. describe ranges of RF signal for creating the ultrasound, ultrasound power density levels, ranges of duration for each ultrasonic pulse, and ranges of ultrasonic pulse frequencies.

U.S. Pat. No. 5,003,965 to Talish et al. relates to an ultrasonic body treatment system having a body-applicator unit connected to a remote control unit by sheathed fiber optic lines. The signal controlling the duration of ultrasonic pulses and the pulse repetition frequency are generated apart from the body-applicator unit. Talish et al. also describes a mounting fixture for attaching the body-applicator unit to a patient so that the operative surface is adjacent the skin location.

It has been demonstrated that the components of acoustic energy that can effect chemical change can be thermal, mechanical (agitational) and cavitational in nature. The largest non-thermal effects are those attributed to stable cavitation and mass transfer. These, in turn, can induce acoustic microstreaming, producing shear stresses on the cellular wall and boundary layer, and in the cytosol. The latter effect, due to intracellular microstreaming, can produce an increase in the metabolic function of the cell.

Since the early sixties, the specific physical and biological mechanisms behind the therapeutic effectiveness of low intensity ultrasound have been extensively investigated. For spatial average-temporal average (SATA) intensities from 0.1–0.5 W/cm$^2$, it is possible to produce the non-thermal, high stress mechanisms of acoustic streaming and cavitation. In vitro tests on isolated fibroblast cells have shown that the effects of ultrasound on the cells are pressure sensitive, suggesting a (stable) cavitation mechanism, caused by the rapid expansion and collapse of microbubbles. The resulting bubble oscillations, possibly including acoustic microstreaming, can generate high shear stress on the cell membrane, which can affect the cell's permeability to sodium and calcium ions. The increase in cell permeability may result in an increase in calcium uptake, an increase in protein and DNA synthesis in fibroblasts, and account for the observed activation of macrophages. The production of fibroblasts and macrophages characterizes the normal fracture repair process.

It has been determined that the cavitation threshold, i.e., the energy required for cavitation, is approximately 0.1 W/cm$^2$ in an aqueous medium and approximately 0.2 W/cm$^2$ in vivo. One in vivo study conducted utilizing a simulated cell membrane attributed the measured ultrasound-induced changes in the properties of cell membranes to changes in diffusion rates produced by fluid layer movement near the membrane. It has also been demonstrated that the value of micromechanical stimuli (0.5 Hz for 17 minutes, daily) significantly improves the healing of tibial fractures. One study was able to correlate this accelerated healing process with the promotion of fracture revascularization. However, for SATA intensities below 0.1 W/cm$^2$, stable cavitation and acoustic micro-streaming seem quite unlikely. In another study, exposure to low intensity ultrasound produced increased levels of aggrecan mRNA in a rat femur model in the early stages of treatment.

In vivo test results indicate that a low SATA intensity from 30–50 mW/cm$^2$ is highly effective in stimulating bone fracture repair. These results support the thesis that ultrasonically-induced mechanical vibrations tend to increase the permeability of the cell membrane.

In other clinical studies, preliminary results indicate that angiogenesis, the development of new blood vessels, is a key component in the initial phase in the cascade of events involved in the bone fracture healing process. The increased vascularity and the micromechanical fluid pressure appear to produce an increase in cellular calcium uptake, resulting in increased protein synthesis, thereby accelerating bone fracture healing and tissue repair.

Accordingly, there is a need for a method and kit for accelerating bone and tissue healing utilizing the scientific and anatomical observations and studies discussed above. That is, there is a need for a method and kit for accelerating bone and tissue healing by lowering the cavitation threshold to a level attainable with low intensity ultrasound to produce acoustic intracellular microstreaming. Since intracellular microstreaming can produce an increase in the metabolic functions, the method and kit would accelerate the healing process.

SUMMARY OF THE INVENTION

The method and kit of the present invention is used for therapeutically treating bone and tissue injuries using low intensity ultrasound. The method includes the steps of introducing an ultrasound contrast agent into the patient, preferably, the patient's blood stream, and impinging ultrasonic waves in proximity to an injury, wherein the ultrasound contrast agent facilitates in lowering the cavitation threshold, i.e., the energy required for cavitation, to a level attainable by the low intensity ultrasonic waves. It is preferred that the ultrasonic waves exhibit an intensity from about 0.1 to 0.5 W/cm$^2$ to produce non-thermal, high-stress mechanisms of acoustic intracellular microstreaming and cavitation.

The present invention also provides a kit for therapeutically treating bone and tissue injuries using low intensity ultrasound. The kit includes an ultrasonic transducer assembly having at least an ultrasonic transducer, a placement module configured to be worn by a patient and to receive the ultrasonic transducer assembly, an integrated ultrasonic signal generator located in the ultrasonic transducer assembly, a main operating unit (MOU) or controller, a pouch constructed to receive the MOU, and an ultrasound contrast agent provided in a syringe or a capsule in sufficient quantity for the treatment time.

Preferably, the MOU has an internal power source for powering the signal generator circuitry, a display coupled to the signal generator circuitry to display treatment sequence data, and a keypad coupled to the signal generator circuitry to permit user operation and/or entry of data. Further, the MOU is fitted within the pouch which is reliably secured to a patient during treatment, thereby providing patient mobility. Timing control circuitry, as well as monitoring circuitry for the proper attachment and operation of the ultrasonic transducer assembly, are also housed within the MOU. A MOU envisioned for use with the present invention is described in U.S. Pat. No. 5,556,372 to Talish et al.; the contents of which are hereby incorporated by reference.

The signal generator circuitry includes a processor, means for generating a pulsed control signal, and a switch coupled to the processor for regulating the pulsed control signal. A communication interface may be connected between a communication port and the processor to provide a communication link between the ultrasonic signal generator and an external computer or modem. Preferably, the communication interface is a serial communication interface, however, a parallel interface is also contemplated. An alarm may be provided to indicate to the user that the treatment time has expired. The alarm is coupled to the processor such that when ultrasonic treatment is completed the processor activates the alarm and terminates ultrasound generation.

In operation, the MOU is electrically coupled to the at least one transducer of the ultrasonic transducer assembly for transmitting signals to the at least one transducer for controlling the same. The ultrasound contrast agent is preferably introduced into the blood stream to induce acoustic intracellular microstreaming to lower the cavitation threshold to a level attainable with the ultrasonic waves to be emitted by the at least one transducer. The at least one transducer is then excited to impinge ultrasonic waves for a predetermined period of time against the trauma site.

It is contemplated that the ultrasonic waves may be emitted away from the trauma site and reflected toward the trauma site by a bone or an implanted inorganic material, such as a metallic plate. It has been demonstrated that the acoustic intracellular microstreaming produces an increase in the metabolic functions of the cell, thereby accelerating the healing process.

BRIEF DESCRIPTION OF THE DRAWINGS

Preferred embodiments of the invention are described below with reference to the drawings, which are described as follows.

DETAILED DESCRIPTION OF THE PREFERRED EMBODIMENTS

Figure 1:
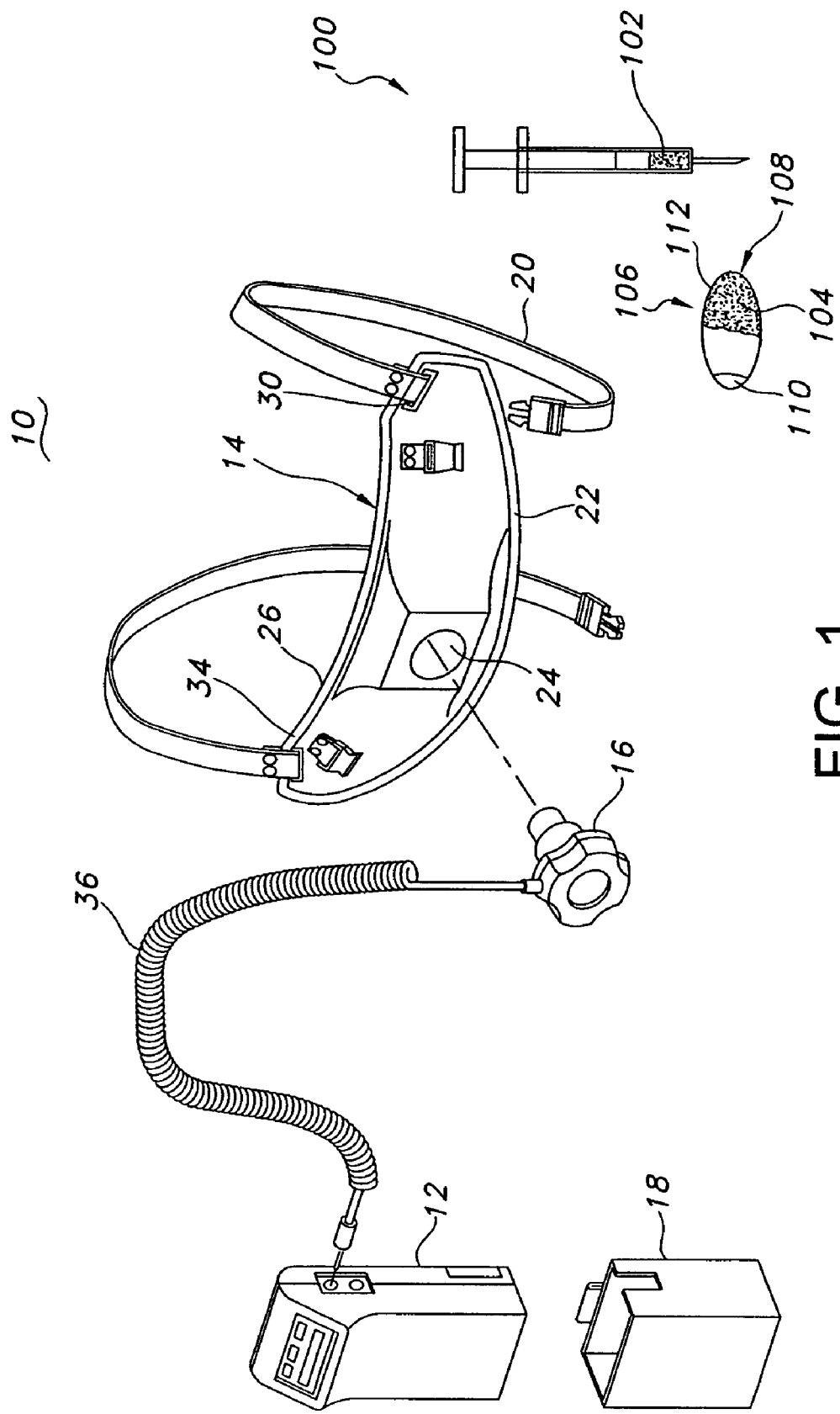
FIG. 1 is a perspective view with parts separated of a portable ultrasonic treatment kit according to the present invention, illustrating a main operating unit or controller, a placement module, an ultrasound contrast agent housed within a syringe, and an ultrasound contrast agent encapsulated in a delivery/release system.

The ultrasonic treatment method and kit of the present invention is used for the surgically non-invasive utilization of low intensity acoustic energy to accelerate the healing process for treating bone and tissue injuries. The present invention uses the concept that the bone fracture and wound healing process can be further enhanced and accelerated if the mechanisms of stable cavitation and microstreaming are induced within the low intensity ultrasound regime. This will have several important biological effects: (1) it will further increase the permeability of the cellular wall membrane, enhancing the diffusion process for calcium uptake and protein synthesis, (2) increase the amount of hemoglobin released, (3) effect the gene expression within the insonated tissue, and (4) assist in the removal of debris from the trauma site.

At the frequencies generally employed for therapeutic and diagnostic ultrasound, from 0.1 MHz to 10 MHz, the cavitation threshold, i.e., the energy required for cavitation, occurs at pressure levels exceeding 5 MPa However, ultrasound contrast agents having gas-filled microbubbles, with radii preferably from 0.4 to 1.0 µm, have been observed to lower the cavitation threshold to less than 0.2 MPa, a factor of more than twenty-five, when targeted or impinged with acoustic energy.

Ultrasound contrast agents are nontoxic, are usually injected intravenously, can pass through the pulmonary, cardiac and capillary circulation systems, increase the backscatter only with high tissue contrast, and recirculate through the systems during a medical examination. Most of the agents consist of gas-filled microbubbles with bubble resonance frequencies in the 0.5 to 10 MHz range which is the frequency range for most therapeutic and diagnostic ultrasound medical applications. Fortunately, these correspond to bubble sizes less than 7.0 microns, small enough to pass through pulmonary, cardiac and capillary circulations. The backscattered energy can be increased by either increasing the contrast concentrations or by causing free air bubbles to resonate within the fluid, producing scattering cross-sections several orders of magnitude larger than their geometric cross-sections.

Clinically, it has been demonstrated that ultrasound contrast agents can significantly enhance the detection of blood flow in small malignant breast tumors, in small deep vessels in the abdomen, help differentiate tumor and normal tissue vascularity, aid in the detection of ischemia or occlusion and improve the visualization of vascular stenosis. Examples of ultrasound contrast agents are Definity™ (Dupont Pharmaceuticals, Bellerica, Mass.), Sonazoid™ (Nycomed-Amersham, Oslo, Norway), Optison™ (Molecular Biosystems, Inc., San Diego, Calif.), Imagent™ (Alliance Pharmaceutical Corp., San Diego, Calif.), and SonoRx™ (Bracco Diagnostics, Princeton, N.J.).

The pressure level at which the cavitation threshold is lowered, by the use of ultrasound contrast agents having gas-filled microbubbles with radii from 0.4 to 1.0 μm, is almost equal to that defined by the spatial peak temporal average (SPTA) acoustic intensity for the Sonic Accelerated Fracture Healing (SAFHST™) ultrasonic transducer manufactured by Exogen, Inc. of Piscataway, N.J. From 1995 to 1999, a set of twenty-one measurements were made of SAFHS™ transducers at a frequency of 1.5 MHz by Sonic Technologies, located in Hatboro, Pa., resulting in a sample mean (far-field) SPTA of 110.34 mW/cm², with an unbiased sample standard deviation of 4.02 mW/cm².

In any given plane in the acoustic field, the SPTA acoustic intensity, I, can be expressed as:

$$I = [\text{Integral of Waveform Squared}] \cdot PRF/K_f^2 \text{ W/cm}^2,$$

where the term in the brackets is essentially the energy in the waveform, PRF is the pulse repetition frequency and $K_f^2$ is often referred to in the literature as the intensity response factor. If the transmitted signal is a pulsed sine wave of rectangular envelope, given by $V(t)=V_o \sin 2\pi f_c t$, with pulse length 2T and carrier frequency $f_c$, then $$I = P_o^2 T(PRF)/(10^4 \rho c) \text{ W/cm}^2,$$

where $P_o$ is the peak pressure in Pascal. The relevant parameters for soft tissue and the SAFHS® transducer are: $\rho=1000$ kg/m³, c=1496 m/s, PRF=1.0 kHz, T=100 μsecs and $f_c$=1.50 MHz, resulting in the following relationship between the peak pressure (in MPa) and SPTA intensity (in mW/cm²) in tissue:

$$P_o = \{0.00015 \times I\}_{1/2} \text{ MPa}.$$

For a duty cycle of 20%, a SATA intensity of 30 mW/cm² results in a SPTA intensity of approximately 97.2 mW/cm², which in turn, results in a peak pressure of 0.12 MPa. Therefore, by introducing microbubbles into the system, a SATA intensity from 80 to 100 mW/cm² can produce peak pressure levels that exceed the cavitation threshold.

In line with the above mathematical relationships, the principles of the present invention entail administering an ultrasound contrast agent having gas-filled microbubbles to a patient and subsequently inducing acoustic intracellular microstreaming by transmitting acoustic energy using an ultrasonic transducer. Accordingly, the kit of the present invention includes an ergonomically constructed placement module having a strap or other fastening means for being secured to an injured part of a patient's body. At least one ultrasonic transducer assembly partially fabricated with a conductive plastic material is attached or imbedded within the placement module and properly positioned in proximity to the trauma site.

Different types of ultrasonic transducers and signals can be provided, such as those described and schematically depicted in U.S. Pat. No. 5,520,612 to Winder et al.; the contents of which are hereby incorporated by reference.

Particularly, the transducers and arrangements schematically depicted by FIGS. 7–11 of the patent in which at least one transducer is used to provide acoustic energy to the site of the injury. The kit also utilizes a portable, ergonomically constructed main operating unit (MOU) which is constructed to fit within a pouch worn by the patient using belt and shoulder strap and provides control signals to the ultrasonic transducers. The MOU which is utilized is preferably the one described in U.S. Pat. No. 5,556,372 to Talish et al.; the contents of which are hereby incorporated by reference.

Turning to the figures, in particular FIG. 1, a preferred embodiment of the portable ultrasonic treatment kit 10 of the present invention is shown. The ultrasonic treatment kit 10 includes a MOU 12, a placement module 14, an ultrasonic transducer assembly 16, a pouch 18 for reliably securing the MOU 12 to the patient during treatment for providing patient mobility, and a syringe 100 housing an ultrasound contrast agent 102 having gas-filled microbubbles. The syringe 100 is used for intravenously introducing the contrast agent 102 into the patient's body, preferably, the patient's blood stream, prior to administering ultrasonic treatment as further described below. The kit 10 further includes a delivery/release system 106 as further described below.

It is contemplated that the microbubbles can be swallowed in capsule form. The capsule can be designed to be timed-release, and the microbubbles released internally at a controlled, designated time. The required capsule, timed-release technology is well known to the pharmaceutical industry (e.g., Andryx Corporation, Fort Lauderdale, Fla., manufactures such timed-release capsules).

The placement module 14 is comprised of placement bands 20 and placement support 22. The placement support 22 includes a pocket 24 adapted for placement of the ultrasonic transducer assembly 16 therein. The placement support 22 further includes a body rest 26 having slots 30 for connecting the placement support 22 to the placement bands 20. A sponge-like material 34 lines the inner surface of the placement support 22 for providing comfort to the patient. The placement support 22 may be construed of hard plastics which may be custom molded for a particular patient.

The transducer assembly 16 includes circuitry, schematically illustrated by FIGS. 4A and 4B and described below, for exciting at least one transducer therein and is coupled to the MOU by cable 36. The cable 36 is preferably a multiconductor cable capable of transmitting relatively low frequency RF or optical signals, as well as digital signals. The cable 36 may include coaxial cable or other types of suitable shielded cable. Alternatively, the cable 36 may include fiber optic cable for transmitting optical signals. The signals may be transmitted continuously or as a series of pulses.

Figure 2:
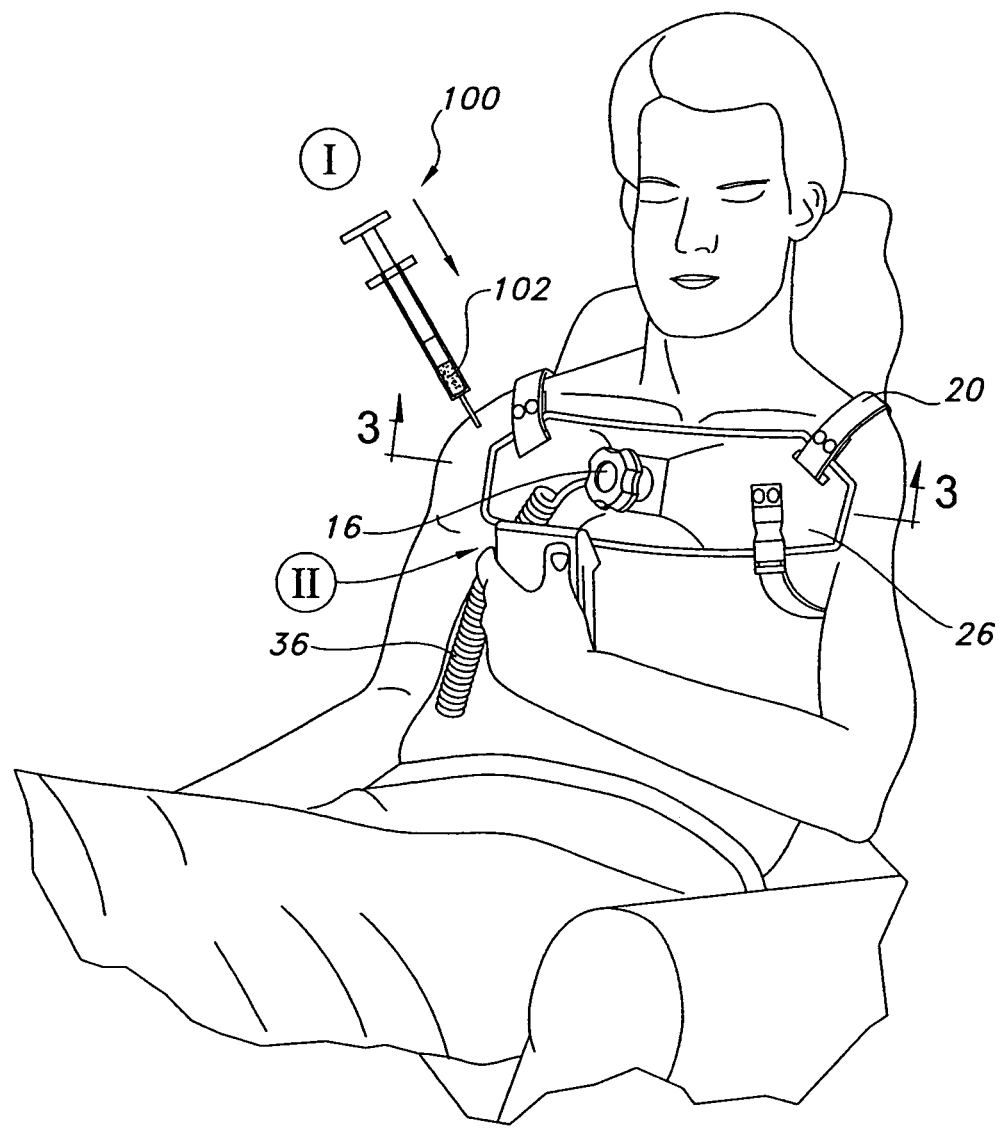
FIG. 2 is a perspective view of a patient wearing the portable treatment apparatus of FIG. 1.

In operation, the placement module 14 is positioned and secured to the patient's body as shown by FIG. 2, such that the transducer assembly 16 lies over or in proximity to an injury. A locating ring such as the one disclosed in U.S. patent application Ser. No. 08/389,148 may be used for determining the location of injured bone in the case of a bone injury before the placement module 14 is secured to the patient. Once the placement module 14 is properly positioned (or prior to being properly positioned), the ultrasound contrast agent 102 having the gas-filled microbubbles is introduced into the patient's body intravenously using the syringe 100 (indicated by step I in FIG. 2). The microbubbles are designed to stay in the system over a period of time from as little as one to at least twenty minutes. The microbubbles act as cavitation nuclei to increase cell membrane permeability and to enhance the angiogenesis process that is part of the cascade of biological events in the tissue healing process.

Figure 3:
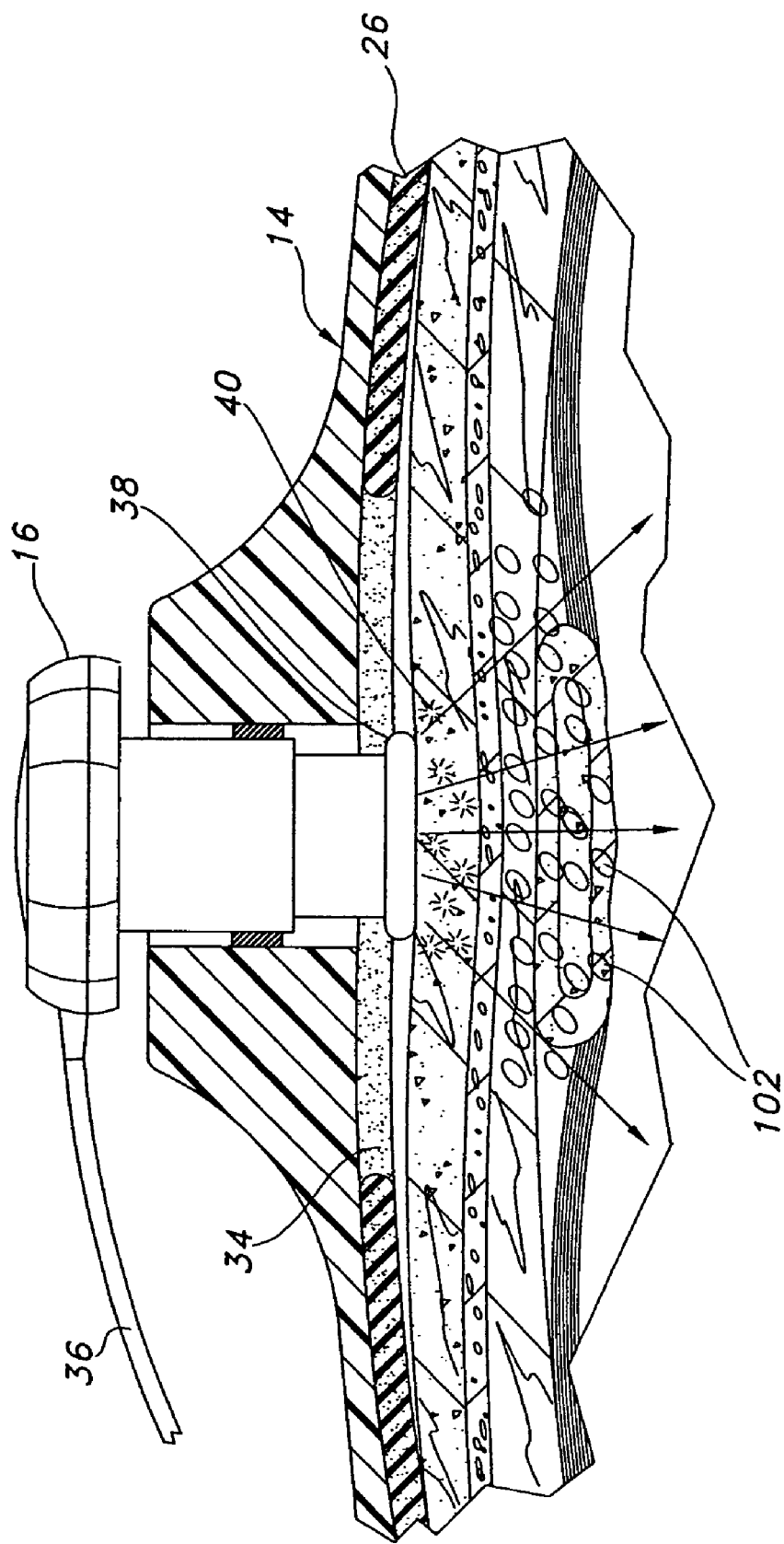
FIG. 3 is a cross-sectional view along line 3—3 in FIG. 2 illustrating the transducer assembly impinging ultrasonic waves after the ultrasound contrast agent has been introduced into the patient.

The transducer within the transducer assembly 16 is then excited for a predetermined amount of time (indicated by step 11 in FIG. 2). A gel-like substance 38 is positioned between the transducer assembly 16 and the injured part of the patient's body to increase the acoustic coupling of the ultrasonic waves emitted from the transducer to the outer skin-soft tissue of the body, as shown by FIG. 3. With the presence of ultrasonic waves, the microbubbles become acoustically active targets with ultrasound insonification, thereby causing cavitation to occur at low pressure levels to accelerate the healing process.

The kit 10 of the present invention permits the bubble resonance frequency, the bubble radii, the SATA intensity and the transmitting frequency of the ultrasonic waves to be controllable to significantly lower the cavitation threshold to levels produced by low intensity ultrasound. For example, the transmit frequency of the ultrasonic waves can be controlled to range from 10 kHz to 10 MHZ, the bubble radii from 0.1 to 10.0 μm, and SATA intensities from about 5 to 500 mW/cm$^2$. It is contemplated that the optimum values for these parameters for a particular patient are predetermined and set accordingly during treatment to achieve optimum healing.

With reference to FIG. 1 and as indicated above, the kit 10 further includes another ultrasound contrast agent 104 in a delivery/release system 106 that facilitates the "targeting" of the agent(s) 104 to a specific location in the body. Delivery/release systems are known in the art. The system 106 has the advantage of delivering the agent(s) 104 precisely to the trauma site for cellular metabolic action to occur.

In its simplest form, the capsule 108 exists without a sensor and associated circuitry, and is configured as a chemically-controlled timed-release system, with contrast agent(s) 104. In a more complex configuration, the delivery/release system 106 is contemplated to have the capsule 108 containing a non-lead piezoelectric sensor 110, such as polyvinylidene fluoride (PVDF), for receiving and responding to an acoustic signal, and a compartment 112 for the contrast agent(s) 104.

During operation, the ultrasonic transducer assembly 16 is applied to the skin of the body at or near the site of the bone fracture or tissue wound and activated to administer the normal therapeutic dosage. The transmitted acoustic signal is detected by the sensor 110 in the capsule 108, thereby releasing a predetermined amount of the contrast agent(s) 104 within the compartment 112 of the capsule 108. It is contemplated that the capsule 108 includes a processor which is programmed by chemical and/or electromagnetic means for releasing the agent(s) 104 at different locations of the body, in preset amounts, at multiple, predetermined time intervals. After total agent release, the remaining part of the capsule 108 is discarded naturally as a waste product.

Figure 4A:
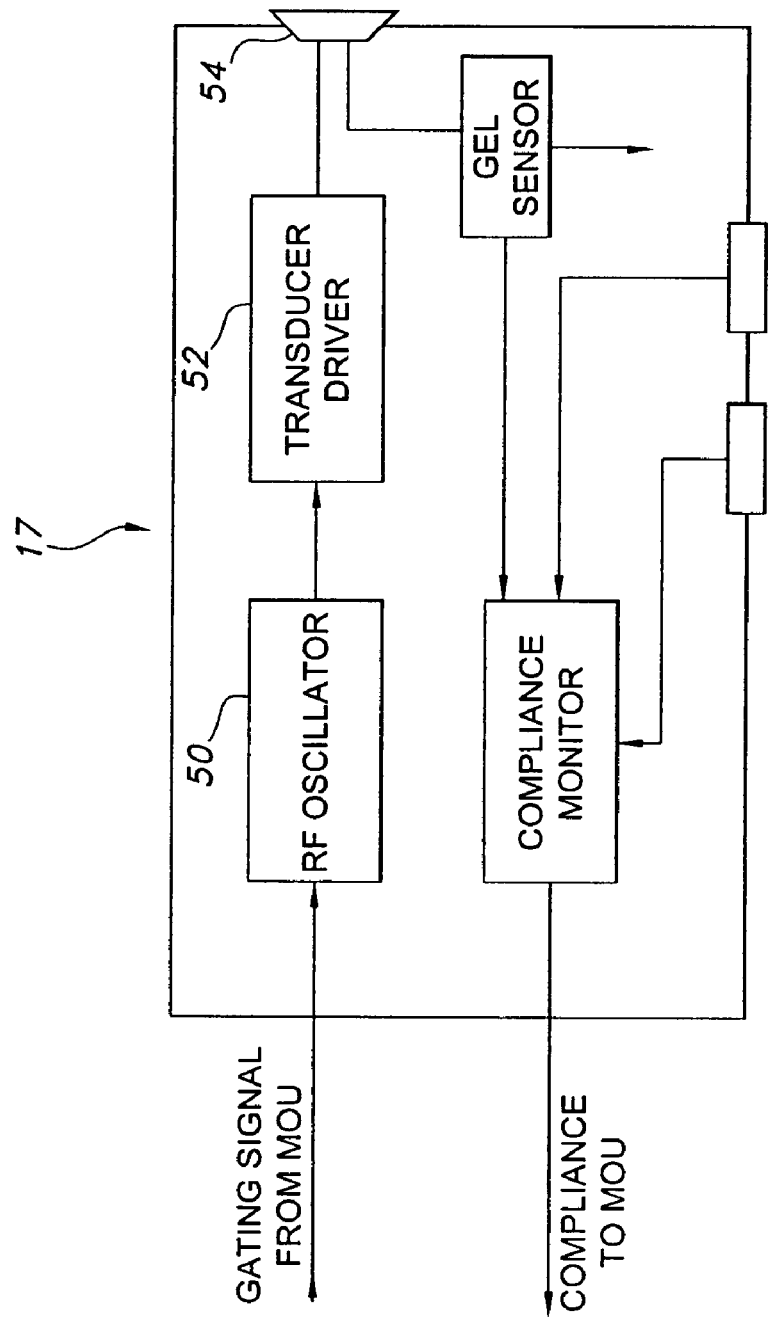
FIG. 4A is a block diagram of one embodiment of the circuitry for the ultrasonic transducer assembly.

With reference to FIG. 4A, a block diagram of one embodiment of the ultrasonic transducer assembly circuitry is shown. The transducer assembly circuitry 17 includes an RF oscillator 50 which receives the signals transferred by a signal generator within MOU 12 via cable 36. RF oscillator 50 is connected to transducer driver 52 which excites transducer 54.

Figure 4B:
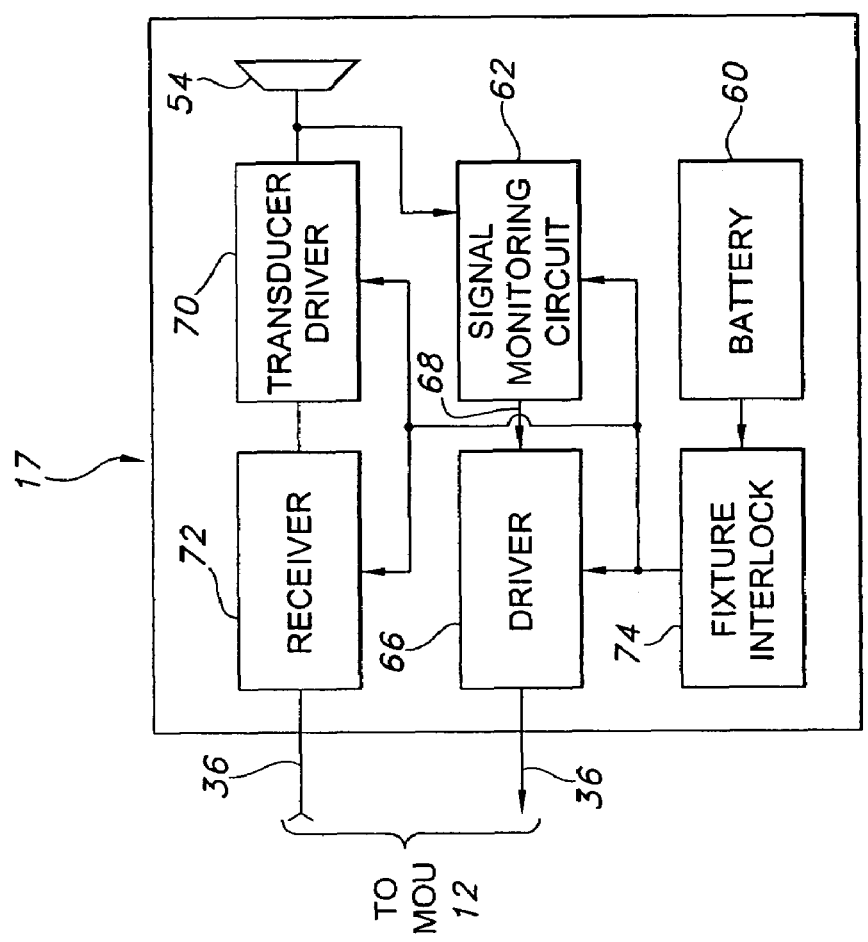
FIG. 4B is a block diagram of an alternative embodiment of the circuitry for the ultrasonic transducer assembly.

An alternative embodiment of the transducer assembly circuitry 17 is shown in FIG. 4B. In this embodiment, the ultrasonic transducer assembly 16 includes an internal battery 60 which supplies power to the components within the transducer assembly 16. For example, battery 60 supplies power to signal monitoring circuit 62 and signal driver 66. The signal monitoring circuit 62 provides, preferably, a digital output signal 68 which represents the waveform characteristics of the output of transducer driver 70. These characteristics can be displayed on a digital display and may include, for example, the frequency, pulse repetition frequency, the pulse width and the average output power of the transducer 54. The output signal 68 of signal monitoring circuit 62 is transferred to the signal generator within MOU 12 via driver 66 and cable 36. The signal generator may include a processor and a switch for regulating the signal characteristics. Control signals from the MOU 12 are received by receiver 72 via cable 36. Safety or fixture interlock 74, which may include switches on the outer surface of the placement module 14 or transducer assembly 16, ensures that the placement module 14 is properly positioned before providing power to the internal components of the transducer assembly 16. That is, fixture interlock 74 prevents inadvertent activation of the transducer assembly 16.

It will be understood that various modifications can be made to the various embodiments of the present invention herein disclosed without departing from its spirit and scope. For example, various methods of introducing the ultrasound contrast agent(s) into the patient's body are foreseen other than intravenously or in capsule form. Also, various modifications may be made in the structural configuration of the placement module and the configuration of the components used to excite the ultrasonic transducer. Therefore, the above description should not be construed as limiting the invention but merely as presenting preferred embodiments of the invention. Those skilled in the art will envision other modifications within the scope and spirit of the present invention as defined by the claims presented below.

What is claimed is:

1. A method for accelerating a healing process for an injury using ultrasound, the method comprising
    introducing a capsule comprising a piezoelectric sensor and an ultrasound contrast agent into a patient, wherein the ultrasound contrast agent is adapted to accelerate a healing process for an injury upon application of ultrasound;
    mounting an ultrasonic source to the patient;
    transmitting an acoustic signal to the piezoelectric sensor instructing the capsule to release a portion of the ultrasound contrast agent, wherein the release of the ultrasound contrast agent is specifically targeted to the proximity of the injury; and
    impinging ultrasonic waves in proximity to the injury, wherein the ultrasound contrast agent facilitates in lowering the cavitation threshold to an intensity level attainable by the ultrasonic waves.

2. The method according to claim 1, further comprising maintaining the acoustic spatial average-temporal average (SATA) intensity of the ultrasonic waves from about 5 to 500 mW/cm$^2$.

3. The method according to claim 1, wherein the ultrasound contrast agent is comprised of microbubbles having a radius from 0.1 to 10.0 um.

4. The method according to claim 3, further comprising maintaining the resonance bubble frequency of the microbubbles from 0.5 MHz to 10 MHz.

5. The method according to claim 3, wherein the radii of the microbubbles of the ultrasound contrast agent are less than 7.0 μm.

6. The method according to claim 1, further comprising maintaining the acoustic transmit frequency of the ultrasonic waves from 10 MHz to 10 MHz.

7. The method according to claim 1, further comprising terminating the impinging step after approximately thirty minutes.

8. The method according to claim 1, wherein introducing a capsule further comprises time-releasing the ultrasound contrast agent into the patient.

9. The method according to claim 1, wherein introducing a capsule further comprises using a syringe to intravaneously introduce the capsule comprising a piezoelectric sensor and an ultrasound contrast agent into the patient.

10. The method according to claim 1, wherein introducing a capsule further comprises using a capsule that is timed-release.

11. The method according to claim 1, wherein transmitting an acoustic signal to the piezoelectric sensor comprises instructing the capsule to release the ultrasound contrast agent in preset amounts at multiple predetermined time intervals.

12. A method for accelerating a healing process for an injury upon application of ultrasound, the method comprising the steps of:
   providing a main operating unit having an internal power source coupled to an ultrasonic transducer assembly, the ultrasonic transducer assembly includes at least one ultrasonic transducer, an ultrasonic signal generator and signal generator circuitry therein, wherein the ultrasonic transducer assembly is adapted to be mounted to a patient's body;
   providing a placement module configured for receiving the ultrasonic transducer assembly and for placing the at least one ultrasonic transducer in proximity to the injury;
   providing a syringe capable of introducing a capsule comprising a piezoelectric sensor and an ultrasound contrast agent into the patient;
   introducing via the syringe a capsule comprising a piezoelectric sensor and an ultrasound contrast agent into the patient, wherein the ultrasound contrast agent is adapted to accelerate a healing process for an injury upon application of ultrasound, and the piezoelectric sensor is capable of receiving an acoustic signal to release at least some of the ultrasound contrast agent inside the patient;
   transmitting an acoustic signal to the piezoelectric sensor instructing the capsule to release a portion of the ultrasound contrast agent in proximity to the injury; and
   exciting the at least one ultrasonic transducer to impinge ultrasonic waves at or near the injury, wherein the ultrasound contrast agent facilitates in lowering the cavitation threshold to an intensity level attainable by the ultrasonic waves.

* * * * *